United States Patent [19]

Clair

[11] Patent Number: 4,483,337
[45] Date of Patent: Nov. 20, 1984

[54] ENDOTRACHEAL TUBE RETAINER AND TUBE SIZE INDICATOR

[76] Inventor: Michael W. Clair, 8806 Willis Ave. #22, Panorama City, Calif. 91402

[21] Appl. No.: 431,335

[22] Filed: Sep. 30, 1982

[51] Int. Cl.$^3$ ............................................. A61M 25/02
[52] U.S. Cl. ................................................ 128/207.17
[58] Field of Search ..................... 128/207.14, 207.15, 128/207.17, 207.18, 205.24, 912, 204.18, 200.21, DIG. 26; 285/401, 93; 251/149.6; 604/174, 177, 179

[56] References Cited

U.S. PATENT DOCUMENTS

| | | | |
|---|---|---|---|
| 3,176,690 | 4/1965 | H'Doubler | 604/174 |
| 3,890,976 | 6/1975 | Bazell et al. | 128/207.15 |
| 4,015,608 | 4/1977 | Rogers | 128/207.17 |
| 4,313,437 | 2/1982 | Martin | 128/207.17 |
| 4,316,459 | 2/1982 | Walski | 128/207.17 |
| 4,331,144 | 5/1982 | Wapner | 121/207.17 |

Primary Examiner—Henry J. Recla
Assistant Examiner—Karin M. Reichle
Attorney, Agent, or Firm—David O'Reilly

[57] ABSTRACT

An endotracheal tube comprised of a tube for placement in the trachea having an inflatable cuff for sealing the trachea on one end and a standard connector adaptor on the other end for securing a breathing tube to supply a gas, such as air, to a patient. A retainer is provided in the form of at least one pair of retaining tabs integrally secured to the exterior surface of the endotracheal tube near the connector end. The tabs are constructed to wrap securely around the tube when not in use, with their respective ends being fastened to one another. To secure the endotracheal tube to a patient after insertion in the trachea, the retaining tabs are unwrapped and a flexible headband is secured to the free ends of the tabs around the head of the patient. Up to two and possibly three sets of retaining tabs are contemplated and may be integrally formed in the exterior surface of the tube. The endotracheal tube will also include a color coded strip near the connector end of the tube, providing an instant indication of the size of the tube. Several various colors will be selected to provide tube size indications in increments of 0.5 millimeters (mm).

7 Claims, 3 Drawing Figures

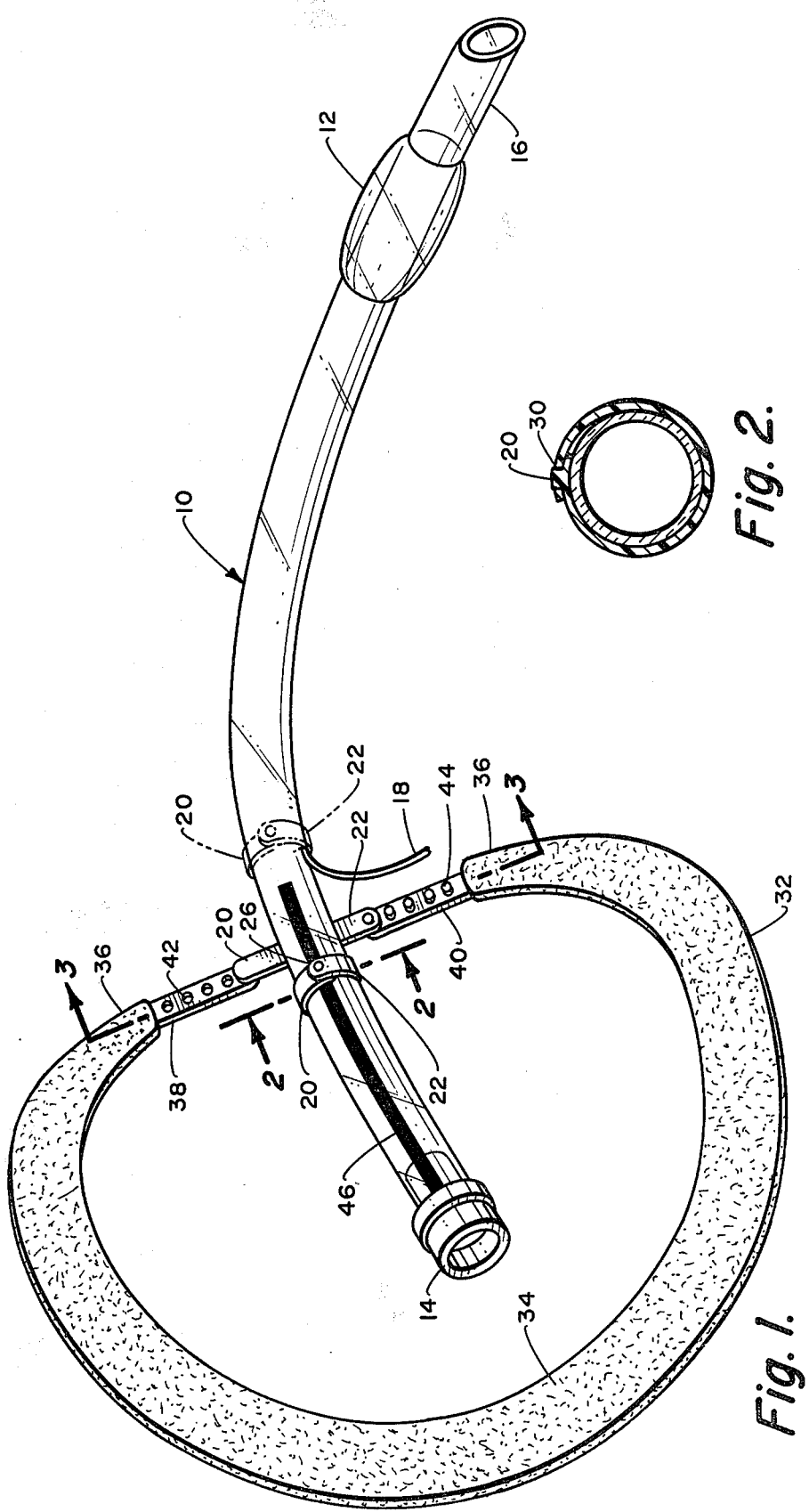
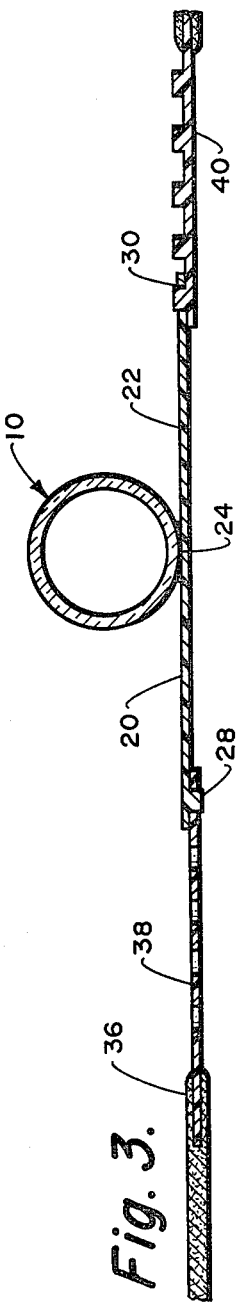

ENDOTRACHEAL TUBE RETAINER AND TUBE SIZE INDICATOR

FIELD OF THE INVENTION

This invention relates to endotracheal tubes and, more particularly, relates to devices for retaining endotracheal tubes in position after placement in a patient.

BACKGROUND OF THE INVENTION

Endotracheal tubes are usually placed in the trachea of the patient, the inflatable cuff expanded to seal the trachea with the connector end extending out of the mouth of the patient. The customary method used to secure the endotracheal tube to a patient is to loop white adhesive tape around the head with the ends being wrapped around the tube at the corner of the mouth. The white adhesive tape, of course, becomes quickly soiled by oral secretions, mucus, blood, and perspiration. However, since it is easily available, inexpensive and a method familiar to everyone, it is used in spite of its inherent problems. That is, irritation of the skin, possible tube displacement during tape change, a media for infection and varied methods of application, many of which are inefficient.

There have been several devices designed for holding an endotracheal tube in position and some are on the market but they all have inherent drawbacks. Generally, the present devices are expensive and cumbersome, leading to poor acceptance by the medical community. Further, the tubes tend to slip through the device no matter how tightly it is fastened because of oral secretions, mucus, blood and perspiration accumulating on these devices. These secretions, in addition to providing an excellent media for infection, also provide organic lubricants which can cause the tube to slip. For that reason the white adhesive tape method is still widely used in spite of its inherent problems.

In the clinical placement of all endotracheal tubes, the pilot line for inflating the external cuff is used as a guide for determining the depth that the tube should be placed in the airway. The endotracheal tube is inserted through the mouth until the place where the pilot line exits the side of the endotracheal tube is at the corner of the mouth and is then secured. The pilot line is therefore frequently referred to as an idiot line, as it supposedly is nearly impossible for anyone to insert the tube to an incorrect depth because they can determine the depth by simply checking the position of this line. However, this method of placing the tube is based on the erroneous, but widely accepted, premise that the distance between the mouth and the vocal cords is uniform in all adults, even though this may not be the case.

Also, in present endotracheal tubes, unless the size is noted before insertion, the tube size cannot be determined except through measurement. Since these tubes are often left in place for days or even weeks at a time, it is frequently necessary to replace a tube which has malfunctioned. This can occur in the form of a leak in the tube or a leak in the inflatable cuff, preventing a proper seal in the trachea. Further, it may be necessary to insert a bronchoscope for diagnostic or therapeutic purposes, thereby requiring removal of the tube. For this reason, knowing the tube size is important.

It is therefore one object of the present invention to provide an endotracheal tube retainer which will eliminate these disadvantages and provide a simple, reliable means of securing the endotracheal tube to the patient.

Another object of the present invention is to provide retaining means in the form of integrally formed tabs as part of the endotracheal tube which are not affected by secretions, need no adhesive tape and is simple and inexpensive to use.

Yet another object of the present invention is to provide several pairs of integrally formed tabs which, when not in use, will wrap around and be secured, closely fitting the outside surface of the tube.

Yet another object of the present invention is to provide a plurality of retaining tabs or flaps along a short length of the tube providing a shorter variation in tube depth adjustment, making the device versatile enough for use by any adult.

Still another object of the present invention is to provide retaining tabs or flaps which, when folded tightly against the tube, will allow the endotracheal tube to be used in a conventional manner without utilizing the tab ties for securing.

Still another object of the present invention is to provide indicating means integrally formed on the surface of the surface of the tube which permits immediate identification of tube size.

SUMMARY OF THE INVENTION

The present invention relates to an endotracheal tube modification which permits simple, reliable placement of the tube and simultaneously gives an indication of tube size without the need for measurement. The endotracheal tube of the present invention is comprised of the usual tube having an inflatable cuff at one end and a standard connection adaptor at the other end for securing a breathing tube to a supply of air or gas. The endotracheal tube is modified in that securing tabs or flaps are provided in pairs of two along the length of the tube nearest the connector or the end which remains externally of the patient. These pairs of tabs wrap securely around the exterior surface of the tube when not in use, allowing the tube to be used conventionally with white adhesive tape, if desired. A pair of tabs can be unwrapped or unfurled from the surface of the tube, permitting attachment of a headband placed around the head of the patient. Preferably the tabs or flaps are integrally attached to the exterior surface of the tube and may be integrally formed when the tube is manufactured. Three pairs of tabs should be sufficient to provide a wide range of variations in tube position adjustment which would make it versatile enough for use with any adult. One set of tabs will be immediately adjacent the exit of the pilot line tube for inflating the cuff with the remaining pair of tabs spaced evenly toward the connector end.

The retaining tabs may be secured by a light adhesive or any other suitable means. However, it is preferred that a pair of tabs have a post and socket arrangement which allow them to be snugly furled or wrapped around the endotracheal tube when not in use. Thus, the tabs not being used will remain closely fitting the outside surface of the tube and not interfere with the tabs and head strap being used.

An indication of the size of the tube is provided in the form of a color coded strip along the longitudinal length of the tube from the connector to approximately the area of the exit of the pilot line. This color coded strip will provide an indication of tube sizes in approximately 0.5 millimeter (mm) sizes. To minimize the number of colors used, full sizes from 6 to 9 millimeters will be indicated by four colors with half sizes 0.5 millimeters larger than full sizes indicated by a broken strip of the same color as the next adjacent whole number. For example, a color code of red could indicate an external diameter of 9 millimeters while a broken strip of red could indicate 9.5 millimeters. In this manner, the range of sizes could be covered with relatively few colors, so that memorizing the color codes for identification purposes will be relatively simple.

The above and other features of the invention will be fully understood from the following detailed description when considered in conjunction with the accompanying drawings, in which:

BRIEF DESCRIPTION OF THE DRAWINGS

FIG. 1 is a perspective view of an endotracheal tube constructed according to the invention.
FIG. 2 is a sectional view taken at 2—2 of FIG. 1.
FIG. 3 is a sectional view taken at 3—3 of FIG. 1.

DETAILED DESCRIPTION OF THE INVENTION

Referring to FIG. 1 there is shown generally the usual endotracheal tube 10 having an inflatable cuff 12 at one end and the usual connection adaptor 14 at the other. The connection adaptor 14 is for the purpose of attaching a breathing tube to supply gas, oxygen or air to the patient through the endotracheal tube.

Typically, the endotracheal tube 10 is inserted through the mouth until the inner end 16 is positioned with the inflatable cuff 12 in the trachea. The inflatable cuff 12 is then expanded via a syringe or other means (not shown) through a pilot line 18 formed in the wall of the tube extending to the inflatable cuff 12. When properly positioned the pilot line 18 will be positioned approximately at the corner of the mouth and the exterior end of the endotracheal tube can be secured.

To secure the endotracheal tube, a pair of retaining tabs 20 and 22 are integrally attached to the exterior surface of the endotracheal tube 10 at 24. In practice, the tabs may be integrally formed as part of the wall on the endotracheal tube 10. Two or three sets of tabs 20 and 22 may be provided along the length of the endotracheal tube in the vicinity of the area where the pilot line 18 exits from the side of the tube. With this many securing tabs provided, a wide variation in the insertion depth or adjustment thereof may be possible, making the endotracheal tube versatile enough for use with any adult.

The ends of the tabs 20 and 22 are formed to overlap slightly at 26 where they can be secured with a light adhesive or by other means. Preferably one tab is formed with a post 28 and the other with a socket 30 so that they can be tightly wrapped around the tube as illustrated in FIG. 2 with the post 28 engaging the socket 30 in the adjacent tab. Thus, when not in use they are tightly furled or wrapped around the endotracheal tube and are out of the way.

As stated previously the securing tabs 20 and 22 may be integrally formed in the surface of the tube or may be one or two pieces attached to the endotracheal tube by means of heat bonding, solvent welding or with an adhesive. If the tab was to be constructed of two pieces, the ends of the tab attached to the tube might be on opposite sides of the tube with each 180° apart. If the tab is constructed of one piece, as is shown, the center of the tab will be secured to the tube as at 24 so that the tabs themselves will extend outward in opposite directions. The tab ends in their normal position are furled or wrapped around the endotracheal tube, as illustrated in FIG. 2. This position may be held as stated previously by the post 28 engaged in the socket 30 or by a small amount of light adhesive on the overlapping ends of the tabs. To use the tabs, the desired tab pairs are simply unfurled or unwrapped and attached to the headband 32 as illustrated in FIGS. 1 and 3. The remaining tabs 20 and 22 may be left furled so as not to interfere with the tube usage or may even be removed if desired.

The endotracheal tube is held at place after placement in the patient by the headband 32, preferably made of an elastic or flexible material. The headband is formed so that the back portion 34 is relatively broad so as to prevent movement and to spread the tension over a larger area. In addition, the ends of the headband tapers as at 36 to a fairly small width and has straps 38 and 40 securely fastened to the ends by sewing, bonding or by some other suitable means. The straps 38 and 40 have sockets 42 and posts 44 which match the respective post 28 and socket 30 in the tabs. Alternately, the tabs could be fastened to the straps 38 and 40 with an adhesive. With the ends of the headband tapering to fastening straps 38 and 40 the fairly small width allows attachment of the tube while still being small enough to allow ready access to the mouth of the patient. In use, the headband would be connected to a securing tab on one end, for example strap 38 connected to tab 20, and the headband brought around the head and then the appropriate strap 40 connected to the tab 22 at the other end. Any extra strap may then be cut off.

Often, after leaving the endotracheal tube in for days, sometimes even weeks, it needs to be replaced because it has malfunctioned; for example, if cuff 12 leaks or the tube itself should malfunction. Also if it is necessary to insert a bronchoscope for diagnostic therapeutic purposes, it is necessary to remove the endotracheal tube and replace it with a fresh tube. Thus, knowing the tube size is extremely important. However, with present endotracheal tubes the only method of determining tube size after removal from the package is by measurement. Since these tube sizes come in increments of 0.5 millimeters, even measurement of some kind is not entirely accurate. Excess size could result in damage or injury to the patient in trying to force an oversize tube into an undersize trachea. Likewise, an undersize tube may require excessive inflation of the endotracheal tube cuff.

For these reasons, a color coding strip has been incorporated into the surface of the tube at the portion that extends outward from the mouth. This color coded strip is indicated at 46 and would extend from the connector 14 to approximately the position where the pilot line 18 exits the side of the tube, in order to be clearly visible. The color coded strip 46 would indicate sizes in increments of 0.5 millimeters from the usual sizes of 6 millimeters up to 9.5 millimeters. In order to minimize the number of colors that need be recognized by a user, solid stripes would indicate whole incremental numbers such as 6 millimeters, 7 millimeters, 8 millimeters and 9 millimeters with broken colors indicating 0.5 millimeters larger than the standard whole number size.

For example, the color coded strip could be in the colors and sizes shown.
  6 millimeters: black
  6.5 millimeters: broken black strip
  7 millimeters: blue
  7.5 millimeters: broken blue strip 8 millimeters: green
8.5 millimeters: broken green strip
9 millimeters: red
9.5 millimeters: broken red strip In this manner eight different sizes can be covered with four easily recognizable and memorized colors. In fact, if the removed endotracheal tube is kept handy, one need only match the color coding to be sure they have the right size without even knowing the size they are actually using. Thus, an easy method of indicating and recognizing the size of endotracheal tubes is provided.

Obviously the invention is not to be limited by the embodiment shown in the drawing and described in the description which is given by way of example and not of limitation but only in accordance with the scope of the appended claims.

What is claimed is:

1. In an endotracheal tube having an inflatable cuff on one end for insertion and sealing in the trachea and a connector at the other end for attachment to a gas supply tube the improvement comprising:

at least one pair of retaining tabs integrally attached to the exterior surface of said endotracheal tube nearest the connector end;

said retaining tabs positioned substantially perpendicular to the longitudinal axis of said tube and being of sufficient length to wrap securely around said endotracheal tube such that the retaining tabs overlap each other when not in use;

a headband;

connector means on the ends of said pair of tabs for connecting said headband;

said means for connecting said headband also constructed to hold said tabs securely in a wrapped position around said tube;

whereby after placement of said endotracheal tube in the trachea said headband holds said tube in place.

2. The endotracheal tube according to claim 1 in which there are three pairs of retaining tabs, said pairs being spaced apart from each other.

3. The endotracheal tube according to claim 1 including a color coded strip on the exterior surface of said endotracheal tube nearest the connector end; said color coded strip indicating the respective tube size.

4. The endotracheal tube according to claim 3 in which said color coded strip indicates tube sizes from 6 mm to 9.5 mm in increments of 0.5 mm.

5. The endotracheal tube according to claim 4 in which there are four colors indicating respectively 6, 7, 8 and 9 mm tubes.

6. The endotracheal tube according to claim 5 in which a broken line of each color indicates a tube size of 0.5 mm greater than the whole number for that color.

7. The endotracheal tube according to claim 1 in which said pairs of tabs have a post on one tab of each pair of tabs and a socket on the other tab of each pair of tabs whereby when they are wrapped around the tube said post on one tab mates with said socket on the other tab.

* * * * *